US009927443B2

(12) United States Patent
Barbosa

(10) Patent No.: US 9,927,443 B2
(45) Date of Patent: Mar. 27, 2018

(54) RISK ASSESSMENT FOR THERAPEUTIC DRUGS

(71) Applicant: Maria D. F. S. Barbosa, Philadelphia, PA (US)

(72) Inventor: Maria D. F. S. Barbosa, Philadelphia, PA (US)

(73) Assignee: ConquerAb Inc., Philadelphia, PA (US)

( * ) Notice: Subject to any disclaimer, the term of this patent is extended or adjusted under 35 U.S.C. 154(b) by 0 days.

(21) Appl. No.: 15/091,483

(22) Filed: Apr. 5, 2016

(65) Prior Publication Data

US 2016/0320405 A1     Nov. 3, 2016

Related U.S. Application Data

(60) Provisional application No. 62/146,232, filed on Apr. 10, 2015.

(51) Int. Cl.
| | |
|---|---|
| *G01N 33/53* | (2006.01) |
| *G01N 33/68* | (2006.01) |
| *G01N 33/543* | (2006.01) |
| *A61B 5/145* | (2006.01) |
| *G05B 15/00* | (2006.01) |
| *G06F 7/06* | (2006.01) |
| *A61B 5/00* | (2006.01) |

(52) U.S. Cl.
CPC ......... *G01N 33/6854* (2013.01); *A61B 5/145* (2013.01); *A61B 5/7275* (2013.01); *G01N 33/54386* (2013.01); *G05B 15/00* (2013.01); *G06F 7/06* (2013.01); *G01N 2800/24* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 3,620,677 A | 11/1971 | Morison | |
| 3,811,840 A | 5/1974 | Bauer et al. | |
| 3,888,629 A | 6/1975 | Bagshawe | |
| 4,042,335 A | 8/1977 | Clement | |
| 4,168,146 A | 9/1979 | Grubb et al. | |
| 4,169,138 A | 9/1979 | Jonsson | |
| 4,219,335 A | 8/1980 | Ebersole | |
| 4,235,601 A | 11/1980 | Deutsch et al. | |
| 4,258,001 A | 3/1981 | Pierce et al. | |
| 4,313,734 A | 2/1982 | Leuvering | |
| 4,348,207 A | 9/1982 | Cappel | |
| 4,366,241 A | 12/1982 | Tom et al. | |
| 4,435,504 A | 3/1984 | Zuk et al. | |
| 4,446,232 A | 5/1984 | Liotta | |
| 4,459,358 A | 7/1984 | Berke | |
| 4,503,143 A | 3/1985 | Gerber et al. | |
| 4,537,861 A | 8/1985 | Elings et al. | |
| 4,594,327 A | 6/1986 | Zuk | |
| 4,623,461 A | 11/1986 | Hossom et al. | |
| 4,624,929 A | 11/1986 | Ullman | |
| 4,632,901 A | 12/1986 | Valkirs et al. | |
| 4,654,309 A | 3/1987 | Milnar et al. | |
| 4,703,017 A | 10/1987 | Campbell et al. | |
| 4,756,828 A | 7/1988 | Litman et al. | |
| 4,770,853 A | 9/1988 | Bernstein | |
| 4,803,170 A | 2/1989 | Stanton et al. | |
| 4,806,311 A | 2/1989 | Greenquist | |
| 4,855,240 A | 8/1989 | Rosenstein et al. | |
| 4,857,453 A | 8/1989 | Ullman et al. | |
| 4,861,711 A | 8/1989 | Friesen et al. | |
| 4,868,108 A | 9/1989 | Bahar et al. | |
| 4,916,056 A | 4/1990 | Brown, III et al. | |
| 4,920,046 A | 4/1990 | McFarland et al. | |
| 4,956,302 A | 9/1990 | Gordon et al. | |
| 4,960,691 A | 10/1990 | Gordon et al. | |
| 4,963,468 A | 10/1990 | Olson | |
| 4,981,786 A | 1/1991 | Dafforn et al. | |
| 4,999,285 A | 3/1991 | Stiso | |
| 5,006,474 A | 4/1991 | Horstman et al. | |
| 5,030,558 A | 7/1991 | Litman et al. | |
| 5,039,607 A | 8/1991 | Skold et al. | |
| 5,075,078 A | 12/1991 | Osikowicz et al. | |
| 5,079,174 A | 1/1992 | Buck et al. | |
| 5,120,504 A | 6/1992 | Petro-Roy et al. | |
| 5,141,850 A | 8/1992 | Cole et al. | |
| 5,164,294 A | 11/1992 | Skold et al. | |

(Continued)

OTHER PUBLICATIONS

Pan et al. (J. Pharm Toxicol. Methods 2011 vol. 63, p. 150-159).*
Shankar et al. Nature Biotechnology 2007 vol. 25, p. 555-561.*
FDA Immunogenicity Assessment for Therapeutic Protein Product (2014).*
Jawa et al. (Clinical Immunology 2013 vol. 149, p. 534-555).*
Stubenrauch et al. (Analytical Biochemistry 2012, vol. 430, p. 193-199).*
Barbosa, M. D. F. S. et al. 2006 Clinical link between MHC class II haplotype and interferon-beta immunogenicity. Clinical Immunology 118: 42-50.

(Continued)

*Primary Examiner* — Changhwa J Cheu

(57) ABSTRACT

Methods to estimate safety and/or efficacy of therapeutic drugs, which include portable devices for anti-drug antibody (ADA) testing and databases containing anonymized data from humans and/or animal models, and related analyses, are provided. These methods and compositions can be used in various applications, including but not restricted to the following: uniform testing of patients for ADA; selection of therapeutic drug for patient treatment; evaluation of the need to change therapeutic drug or to apply tolerance regimens; selection of patients for clinical trials; comparison of therapeutic drugs marketed for a given disease and also gene therapy; scientific guidance for discovering and/or developing therapeutic drugs; postmarketing surveillance of therapeutic drugs.

11 Claims, 6 Drawing Sheets

(56) References Cited

U.S. PATENT DOCUMENTS

| | | | |
|---|---|---|---|
| 5,248,619 A | 9/1993 | Skold et al. | |
| 5,356,782 A | 10/1994 | Moorman et al. | |
| 5,753,497 A | 5/1998 | Bernstein et al. | |
| 5,939,331 A | 8/1999 | Burd et al. | |
| 6,485,982 B1 | 11/2002 | Charlton | |
| 9,377,458 B2* | 6/2016 | Plavina | G01N 33/566 |
| 9,477,811 B2* | 10/2016 | Drucker | A61B 5/743 |
| 2006/0051358 A1 | 3/2006 | Banchereau et al. | |
| 2008/0112852 A1* | 5/2008 | Neel | G01N 33/48771 422/82.01 |
| 2010/0009389 A1* | 1/2010 | Khan | G01N 33/54306 435/7.9 |
| 2012/0063652 A1* | 3/2012 | Chen | G01N 21/274 382/128 |
| 2013/0330724 A1 | 12/2013 | Chen et al. | |
| 2013/0344621 A1 | 12/2013 | Wang et al. | |
| 2015/0226758 A1* | 8/2015 | Grabert | G01N 33/94 506/9 |

OTHER PUBLICATIONS

Barbosa, M. D. F. S. 2011 Immunogenicity of biotherapeutics in the context of developing biosimilars and biobetters. Drug Discovery Today 16: 345-353.

Barbosa, M. D. F. S. et al. 2012 Addressing drug effects on cut point determination for an anti-drug antibody assay. Journal of Immunological Methods 384: 152-156.

Barbosa, M. D. F. S. et al. 2013 Altering drug tolerance of surface plasmon resonance assays for the detection of anti-drug antibodies. Analytical Biochemistry 441: 174-179.

Barbosa, M. D. F. S. and Smith, D. D. 2014 Channeling postmarketing patient data into pharmaceutical regulatory systems. Drug Discovery Today 19: 1897-1912.

FDA approved abel for SOLIQUA (2016).

FDA approved label for TYSABRI (2004).

Gina Kolata. When the Immune System Thwarts Lifesaving Drugs. The New York Times, May 15, 2017.

* cited by examiner

FIG. 3

| 1-Therapeutic drug | 2-Anti-IFN-β incidence[a] (other sources) | 3-Anti-IFN-β incidence[b] (ADA portable device) | 4-HLA link with ADAs[a] | 5-HLA link with ADAs[b] | 6-Protein sequence modification | 7-CMC factors |
|---|---|---|---|---|---|---|
| Pelgridy® (PEG-IFN-β1a; biobetter of Avonex®) | <1%[c] | Portable device ADA data (PDAD) | ND | Test with PDAD | PEG conjugated | ND |
| Avonex® (IFN-β1a) | 1.8% - 7.5%[c] | PDAD | DRB1*0401 DRB1*0408 | | NA | ND |
| Rebif® (IFN-β1a) | 22% - 35%[c] | PDAD | DRB1*0401 DRB1*0408 | Test with PDAD | NA | ND |
| Betaseron® (IFN-β1b) | 22% - 44%[c] | PDAD | DRB1*0701 DRB1*0401 DRB1*0408 | Test with PDAD | C17S mutation; lacks initial methionine | Aggregation; non-glycosylated |
| Biosimilar of Avonex® | ND | PDAD | ND | Test with PDAD | NA | ND |
| Biosimilar to Rebif® | ND | PDAD | ND | Test with PDAD | NA | ND |
| Biosimilar to Betaseron® | ND | PDAD | ND | Test with PDAD | C17S mutation; lacks initial methionine | ND |
| Non IFN-β MS therapies | NA | PDAD | NA | Test with PDAD | NA | ND |

FIG. 4

| 1- Therapeutic drug | 2- Anti-insulin ADA incidence (portable device) | 3- HLA link with ADAs | 4- Protein sequence modifications | 5- CMC factors |
|---|---|---|---|---|
| Humulin® R | Portable Device ADA Data (PDAD) | Test with PDAD | NA | *Escherichia coli* production; ND |
| Humulin® N | PDAD | Test with PDAD | NA | *Escherichia coli* production; ND |
| Humalog® (insulin lispro; fast acting) | PDAD | Test with PDAD | Lys (B28), Pro (B29); amino acids at positions 28 and 29 of the insulin B-chain are reversed | *Escherichia coli* production; ND |
| Levemir® (insulin detemir; long-acting) | PDAD | Test with PDAD | Threonine at posiiton B30 ommited; C14 fatty acid chain attached to amino acid B29 | *Saccharomyces cerevisiae* production followed by chemical modifications; ND |
| NovoLog® (insulin aspart; fast-acting) | PDAD | Test with PDAD | Proline replaced by aspartic acid at position B28 | *Saccharomyces cerevisiae* production; ND |
| Lantus® (insuling glargine; long-acting) | PDAD | Test with PDAD | Asparagine replaced by glycine at position A21 and two arginines added at terminus of B-chain | *Escherichia coli* production; ND |

RISK ASSESSMENT FOR THERAPEUTIC DRUGS

CLAIM OF PRIORITY

This application claims priority to U.S. Provisional Patent Application No. 62/146,232 filed on Apr. 10, 2015, which is hereby incorporated by reference in its entirety.

FIELD OF THE INVENTION

The present invention relates to methods for anticipation, prevention and evaluation of undesirable immune responses against therapeutic drugs, and their applications. More specifically, the present invention relates to compositions for detecting anti-drug antibodies (ADAs), compiling analyses, and deriving scientific knowledge in the fields of oncology, autoimmune diseases (including but not restricted to diabetes, multiple sclerosis and rheumatoid arthritis), cardiovascular diseases, rare diseases, and other diseases for which treatment comprises administration of a therapeutic drug and/or gene therapy.

BACKGROUND OF THE INVENTION

Therapeutic drugs (thereafter also referred to as "drug" or "drugs") can be either natural products, or small molecule drugs, or peptides, or therapeutic proteins (biotherapeutics), or small-molecule-biotherapeutic conjugates (Barbosa, M. D. F. S. et al. 2002 Anal. Biochem. 306: 17-22; Barbosa, M. D. F. S. and Smith, D. D. 2014 Drug Discov. Today. 19: 1897-1912; Grunfeld, C. et al. 2011 Nat. Rev. Drug Discov. 10: 95-96; Kozlowski, S. et al. 2011 N. Engl. J. Med. 365: 385-388; Lee, S. et al. 2013 Nat. Biotechnol. 31: 220-226; Woodcock, J. et al. 2007 Nat. Rev. Drug Discov. 6: 437-442; all expressly incorporated by reference herein). Combination therapies (in which more than one molecular entity is used) are also common.

In attempts to improve efficacy and/or to protect intellectual property positions, several new versions of marketed therapeutic drugs have been developed. In some instances, the novelty consists of introducing mutations to existing drugs. For example, several new insulins are now available for treatment of diabetes, which contain mutated protein sequences relative to native insulin. Protein mutations may significantly alter the drug properties (including but not restricted to aggregation propensity), and may also create epitopes involved in T cell activation and anti-drug antibody (ADA) responses (Barbosa, M. D. F. S. et al. 2006. Clin. Immunol. 118: 42-50; expressly incorporated by reference herein). Unwanted immunogenicity is also a concern for biosimilar versions of marketed protein drugs, typically requiring postmarketing surveillance Besides human genetics, many other factors may be involved in ADA responses against biotherapeutics, such as protein aggregation, sub-visible particles, route of administration, dose, glycosylation, amino acid composition of the protein (and the existence of protein epitopes that can bind to HLA molecules), impurities and others (Barbosa M. D. F. S. et al. 2012 Drug Discov. Today 17: 1282-1288; van Beers, M. M. C. et al. 2011 Pharm. Res. 28: 2393-2402; expressly incorporated by reference herein). Hence, biotherapeutics with identical amino acid sequences may trigger different host immune responses, which may also be dependent on the host genetic makeup (Barbosa, M. D. F. S. and Smith, D. D. 2014 Drug Discov. Today 19: 1897-1912; expressly incorporated by reference herein).

ADAs may impact safety and/or efficacy of therapeutic drugs. It should be noted that loss of efficacy due to ADAs can also be problematic for drug development. One such example is axokine, a modified form of ciliary neurotrophic factor that had been in development for obesity treatment. It was detected during phase 3 clinical trials that 70% of the patients developed anti-axokine ADAs, which decreased efficacy of the drug, ultimately leading to discontinuation of axokine development (Korner, J. and Aronne, L. J. 2004 J. Clin. Endocrinol. Metab. 89: 2616-2621; expressly incorporated by reference herein).

Hosts such as humans and test animals can also mount ADA responses against molecules other than therapeutic proteins. For example, anti-polyethylene glycol (anti-PEG) ADAs have been often observed when hosts are dosed with therapeutic drug-PEG conjugates (Barbosa, M. D. F. S. et al. 2013 Anal. Biochem. 441: 174-179; Judge, A. et al. 2006 Mol. Ther. 13: 328-337; Verhoef, J. F. et al. 2014 Drug Discov. Today 12: 1945-1952; all expressly incorporated by reference herein). Furthermore, the ADAs may be specific for drug degradation products.

A competent host immune system may mount unwanted responses to therapeutic drugs, such as the formation of neutralizing and/or non-neutralizing ADAs and/or various types of hypersensitivity (Barbosa, M. D. F. S. and Smith, D. D. 2014 Drug Discov. Today. 19: 1897-1912; expressly incorporated by reference herein). Host immune reactions often play an important role in adverse effects of therapeutic drugs. Various adverse reactions can result from the use of therapeutic drugs, for example life-threatening IgE- or IgG-mediated anaphylaxis or anaphylactic shock (Barbosa, M. D. F. S. and Smith, D. D. 2014 Drug Discov. Today. 19: 1897-1912; expressly incorporated by reference herein). Although immunogenicity may be associated with all drug classes, the main focus has been in immunogenicity of biologic drugs, likely due to their documented magnitude compared to immunogenicity of small molecules (Barbosa, M. D. F. S. and Smith, D. D. 2014 Drug Discov. Today. 19: 1897-1912; expressly incorporated by reference herein). ADAs may cause clinical syndromes ranging from mild hypersensitivity reactions to life-threatening responses, and may also decrease efficacy of the drug by directly neutralizing activity or by increasing drug clearance (Barbosa, M. D. F. S. and Smith, D. D. 2014 Drug Discov. Today. 19: 1897-1912; Rosenberg, A. S. 2003 Dev. Biol. [Basel] 112: 15-21; Woodcock, J. et al. 2007 Nat. Rev. Drug Discov. 6: 437-442; all expressly incorporated by reference herein).

Antibodies (also named immunoglobulins) are proteins that bind a specific antigen. In mammals such as humans and mice, antibodies contain paired heavy and light polypeptide chains. Standard antibody structural units typically comprise a tetramer. Each tetramer is usually composed of two identical pairs of polypeptide chains, each pair having one "light" (typically having a molecular weight of about 25 kDa) and one "heavy" chain (typically having a molecular weight of approximately 50 kDa). "Isotype" as used herein is meant any of the subclasses of immunoglobulins. The known human antibody isotypes are IgG1, IgG2, IgG3, IgG4, IgA1, IgA2, IgM1, IgM2, IgD, and IgE.

Each antibody chain contains a variable and a constant region, as described above. The variable regions of the light and heavy chains are required for binding the target molecule (the antigen). All ADAs are capable of binding to a target molecule, and hence are referred to as binding antibodies.

An ADA that blocks or diminishes activity of the target protein is designated as a neutralizing antibody, commonly abbreviated to NAb (Shankar, G. et al. 2014 AAPS J. 16: 658-673; expressly incorporated by reference herein). While some IgM can be neutralizing, usually most neutralizing ADAs (NAbs) are of the IgG type.

The following Igs are typically observed in higher mammals: IgD, IgA, IgE, IgM and IgG. IgD amounts to a small percentage of total serum Igs (less than 1%); IgA and IgM can comprise approximately 10-20%. IgG is the predominant Ig in blood. IgM is generally known as the early antibody, as it precedes the IgG response. A draft guidance document issued by the U.S. Food and Drug Administration (FDA) in 2009, recommends that ADA assays should be able to detect all isotypes, particularly immunoglobulin M (IgM) and the different immunoglobulin G (IgG) isotypes.

Host antibody responses against an antigen are typically polyclonal, comprising immunoglobulins that bind the antigen with various affinities and/or avidities. Hence, the assays used to detect antibody responses against therapeutic drugs are inherently qualitative, because there is no positive control antibody that would accurately represent all diverse antibodies in each of the samples collected from diverse sources and/or at various times following antigen exposure.

Product failure greatly increases the cost of developing new drugs, as the industry may incorporate the cost of many drugs that fail during development into the high costs of the few drugs that are approved. Hence, there is considerable interest in predicting and mitigating immunogenicity of biotherapeutics during preclinical discovery and development. Therefore, several attempts have been made to predict immunogenicity of therapeutic proteins during discovery and preclinical development, in particular predictions based on the protein T cell epitope content ("T cell epitope" here defined as amino acid sequences capable of binding to MHC molecules).

Despite those efforts to predict immune responses based on the protein T cell epitope content, it is not possible to ascertain in vitro and without clinical data how the drug will perform in humans. In fact, there are known examples of preclinical immunogenicity predictions that were not confirmed with clinical data (Stickler, M. et al. 2004 Genes Immun. 5: 1-7; Barbosa, M. D. F. S. et al. 2006 Clin. Immunol. 118: 42-50; Barbosa, M. D. F. S. and Celis, E. 2007 Drug Discov. Today. 12: 674-681; Barbosa, M. D. F. S. 2011 Drug Discov. Today 16: 345-353; all expressly incorporated by reference herein). Attempts to predict protein immunogenicity in the absence of clinical data based on protein MHC epitope content may be misleading, as in vivo tolerance and immunogenicity mechanisms may share similar determinants (Barbosa, M. D. F. S. and Celis, E. 2007 Drug Discov. Today 12: 674-681; Couzin, J. 2004 Science 305: 772-; Chaudhry, A. et al. 2009 Science 326: 986-991; Munn, D. H. et al. 2002 Science 297: 1867-1870; Pan, F. et al. 2009 Science 325: 1142-1146; all expressly incorporated by reference herein).

A much more reliable estimation of the likelihood of immune reactions against a therapeutic protein can be based on methods resulting from the composition of clinical data, which can be used for example for statistical analyses of associations between ADA responses and other factors. In order to incorporate a human data-driven approach to immunogenicity prediction and mitigation, methods and processes are needed to systematically harvest and utilize clinical data. Such methods can also be used in conjunction with non-clinical data, and are within the scope of the present invention.

The major histocompatibility gene complex (MHC) is a group of genes that code for proteins involved in immune recognition of foreign substances. In humans, the MHC complex is also named the human leukocyte antigen (HLA) system. The two main types of MHC proteins are MHC class I and MHC class II, and they are very polymorphic cell-surface molecules. The T cell receptor (TCR) recognizes peptides bound to MHC I or MHC II molecules. Antibodies are produced by activated B cells that proliferate and differentiate into antibody producing plasma cells. B cell activation can be dependent or not of T cells. T-independent antigens activate B cells without the need for T-cell help (Zeng, M. et al. 2014 Science 346: 1486-1492). T-dependent antigens are taken up by antigen processing cells, processed and presented (bound to MHC class II molecules) to helper T cells which are involved in B cell activation (Barbosa, M. D. F. S. 2011 Drug Discov. Today 16: 345-353). The human gene complex coding for MHC class II proteins includes three loci (DR, DQ and DP), each containing genes coding for the alpha and beta subunits of an MHC molecule. Following uptake and processing of a protein by antigen presenting cells (for example, dendritic cells), antigenic peptides bound to MHC class II molecules are presented at the cell surface. The peptide bound to the MHC protein forms a complex with a T cell receptor, causing activation of T cells, and ultimately antibody production by differentiated B-cells. That process is also dependent on interactions between co-stimulatory molecules, for example CD28 and CD80/CD86. MHC proteins can vary in their antigen binding specificities; hence, depending on their HLA type, individuals may respond differently to the same antigen (Barbosa, M. D. F. S. and Celis, E. 2007 Drug Discov. Today 12: 674-68; expressly incorporated by reference herein).

Isotype switching and the IgG response are generally T cell dependent, and hence can be associated with specific Human Leukocyte Antigen (HLA) types (Barbosa, M. D. F. S. et al. 2006 Clin. Immunol. 118: 42-50; Barbosa, M. D. F. S. and Celis, E. 2007 Drug Discov. Today. 12: 674-681; Barbosa, M. D. F. S. 2011 Drug Discov. Today 16: 345-353; all expressly incorporated by reference herein). For example, by testing plasma and genetic material of patients treated with Betaseron® (an interferon-β therapeutic protein), it was shown that the major histocompatibility complex (MHC) class II allele DRB1*0701 is associated with anti-interferon-β (anti-IFN-β) ADAs of the IgG type (Barbosa, M. D. F. S. et al. 2006 Clin. Immunol. 118: 42-50; expressly incorporated by reference herein). Even when patients treated with three different IFN-β formulations were evaluated in a large clinical study, strong associations were observed between HLA types (HLA-DRB1*0401 and HLA-DRB1*0408) and ADAs (Hoffmann, S. et al. 2008 Am. J. Hum. Gen. 83: 219-227; expressly incorporated by reference herein). HLA class II binding epitopes can thus activate T helper cells leading to immune responses (Barbosa, M. D. F. S. et al. 2006 Clin. Immunol. 118: 42-50; Barbosa, M. D. F. S. and Celis, E. 2007 Drug Discov. Today 12: 674-681; Tatarewicz, S. M. et al. 2007 J. Clin. Immunol. 27: 620-627; Dalum, I. et al. 1997 Mol. Immunol. 34: 1113-1120; all expressly incorporated by reference herein). It should be noted that in some instances protein epitopes may activate regulatory T cells, which are involved in self-tolerance (Barbosa, M. D. F. S. and Celis, E. 2007 Drug Discov. Today 12: 674-681; De Groot, A. S. et al. 2008 Blood 112: 3303-3311; all expressly incorporated by reference herein). Genetic components other than HLA types may also be immunogenicity determinants (Magdaleine-Beuzelin, C. et al. 2009. Pharmacogenet. Genomics 19: 383-387; Tatarewicz, S. M. et al. 2012. J. Immunol. Methods 382: 93-100; expressly incorporated by reference herein).

In another embodiment, analyses and data in the databases of the present invent can allow determinations of modifications leading to host tolerance to protein drugs (i.e., absence of host immune responses against the drug).

HLA typing of patients treated with Betaseron® and analysis of genetic associations with ADAs has been performed (Barbosa et al, 2006 "Clinical link between MHC class II haplotype and interferon-β (IFN-β) immunogenicity" Clin. Immunol. 118: 42-50; expressly incorporated by reference herein), but to date this has not been a common procedure. Challenges associated with implementation of those association analyses included lack of standardization of ADA assays to be used for identifying genetic associations with ADA responses across products. It should be noted that excluding patients likely to mount ADA responses against a given biotherapeutic might decrease industry profits for that particular therapeutic drug. Hence, in some instances economic drivers may not favor immunogenicity risk assessment if performed by the same industry which profits from the biotherapeutic in question (Barbosa, M. D. F. S. and Smith, D. D. 2014 Drug Discov. Today 19: 1897-1912; expressly incorporated by reference herein).

Another difficulty associated with monitoring ADAs for approved products is the cumbersome nature of collecting patient blood and shipping samples (commonly plasma or serum after blood processing) under special conditions to labs approved for such testing, and the lack of unified methodologies at such laboratories. In addition, such procedures are expensive and time-consuming, and in many instances laboratories offering those services are not even available and/or not known to physicians and/or patients. What follows is that there is an unmet need for available methods and devices to readily detect ADAs and to perform risk assessment for biotherapeutics. Such systems and methods can have several utilities, including but not restricted to stratification of patients likely to benefit from a given therapy, comparison of similar products marketed for the same indication, guidance for new product development, tests during clinical trials, and postmarketing surveillance. Currently it is common practice to indicate in the label of approved biotherapeutics that it would be misleading to compare immunogenicity data with other products, due to differences in assays, and lack of standardization of sample handling and collection and ADA detection for different therapeutic drugs. In addition, specifics of the assays used to detect ADA during clinical trials are typically not disclosed in the product labels (Barbosa, M. D. F. S. and Smith, D. D. 2014 Drug Discov. Today 19:1897-1912; Expressly incorporated by reference herein). Those challenges are becoming increasingly complex, as a growing number of products are approved by regulatory agencies, including but not restricted to biosimilars (a biosimilar is a biotherapeutic similar to another one already marketed for which the patent has expired) and modified versions of marketed biotherapeutics. Although monitoring ADAs is typically a regulatory requirement for development and approval of protein drugs, it is difficult to unify testing procedures for all the drugs approved. During the development of a biosimilar, the same assay may be used to test ADA for comparison of the biosimilar with the reference product, although often there is no systematic postmarketing testing of the reference product. Importantly, in other situations there have been no mechanisms in place to compare systematically therapeutic drugs approved for the same application regarding their immunogenicity in humans, and one of the difficulties is that the assays used vary from one product to the other (Barbosa, M. D. F. S. and Smith, D. D. 2014 Drug Discov. Today 19: 1897-1912; expressly incorporated by reference herein).

The difficulties associated with implementation of current approaches to postmarketing assessment of therapeutic drugs has been reviewed (Barbosa, M. D. F. S. and Smith, D. D. 2014 Drug Discov. Today 19: 1897-1912; expressly incorporated by reference herein). It can be anticipated that the need for comparing traditional drugs with gene therapy will further add to those challenges (Gaudet, D. et al. 2012 Curr. Opin. Lipidol. 23: 310-320; Bennett, J. et al. 2012. Sci. Transl. Med. 4: 120ra115; Nathwani, A. C. et al. 2011 N. Engl. J. Med. 365: 2357-2365; Wang, J. et al. 2008 Nat. Biotechnol. 26: 901-908; Banugaria, S. G. et al. 2011 Genet. Med. 13: 729-736; all expressly incorporated by reference herein). The US Food and Drug Administration has recently initiated an active surveillance system ("the Sentinel Initiative"), which has been defined by the Brookings Institution as "a national, integrated, electronic system for active surveillance of medical product safety that utilizes the capabilities of multiple, existing data systems" (Behrman, R. E. et al. 2011 N. Eng. J. Med. 364: 498-499; Platt, R. et al. 2012 Pharmacoepidemiol. Drug Saf. 21[Suppl. 1]: 1-8; Platt, R. et al. 2009 N. Eng. J. Med. 361: 645-647; all expressly incorporated by reference herein). However, one of the challenges associated with some aspects of drug comparisons with that system is that, in many cases, various different assays are used, resulting in data that is not amenable to the computational analysis.

Pre-existing ADAs (which are present in patients prior to their dosing with a therapeutic drug) may be a risk factor for the development of NAbs (Barbosa, M. D. F. S. and Smith, D. D. 2014 Drug Discov. Today 19: 1897-1912; expressly incorporated by reference herein). An anonymized database containing HLA types and their associations with ADA responses, and also other genetic information, can be used in connection with ADA detection to predict risk of ADA development, as described in embodiments of this invention. In other words, whether pre-existing ADAs are detected or not, the physician and/or patient can access a database for information with anonymized genetic information. Either one of those factors (ADAs or genetics) could indicate risk, with a combination of factors indicating even greater risk.

With a plethora of therapeutic drugs being approved for the same indication, it is becoming increasingly complex for physicians and patients to select the medication likely to provide most benefits (Downing, N. S. et al. 2014 JAMA. 311: 368-377; expressly incorporated by reference herein). For instance, several formulations of interferon-β (IFN-β) are marketed (Rebif®, Betaseron®/Betaferon®, Avonex®, and Pelegridy®), and recently IFN-β biosimilars are also being approved (Barbosa, M. D. F. S. and Smith, D. D. 2014 Drug Discov. Today 19: 1897-1912; expressly incorporated by reference herein). Readily available methods and devices to detect ADAs and perform risk assessment can allow effective comparison of similar products marketed for the same indication, or to compare different products regarding suitability for specific patients.

Establishing the correct dosing of a therapeutic drug that would elicit optimal benefits with acceptable safety profile is also challenging, and selection of dose to be administered to patients is often done during phase 1 clinical trials (dose escalation studies), with a limited number of human subjects. Being able to use the minimal amount of drug that enable the benefits sought is highly desirable, both from the perspective of patient safety and healthcare costs. Many treatments are very expensive (including but not restricted to enzyme replacement therapies and cancer therapeutics), with the drug price often established for mg amounts of the drug. In cases when the patients have pre-existing antibodies against the test therapeutic drug, a higher dose may be required to compensate for the NAb effect; hence, methods and compositions to readily screen patients are also highly desirable from a dose selection perspective (Barbosa, M. D. F. S. and Smith, D. D. 2014 Drug Discov. Today. 19: 1897-1912; expressly incorporated by reference herein).

ADA incidence against chronically administered products such as insulin and enzyme replacement therapies is also a concern. Even if the drug dosage is increased to compensate for NAbs, the chronic administration may results in immune complexes not being cleared, leading to immune complex disease and/or other syndromes (Barbosa, M. D. F. S. and Smith, D. D. 2014 Drug Discov. Today 19: 1897-1912; expressly incorporated by reference herein). In such cases, knowledge of ADA incidence and monitoring can provide an effective mechanism to evaluate risk and the need for tolerance induction regimens (Messinger, Y. H. et al. 2012 Genet. Med. 14: 135-142; expressly incorporated by reference herein). This can be further complemented by knowledge of associated genetic components. Methods to assess risk of immune responses can also be useful to guide therapies other than the ones requiring chronic administration (Ritter, G. et al. 2001 Cancer Res. 61: 6851-6859; expressly incorporated by reference herein).

Although the relevance of preventing and monitoring undesirable human immune reactions against therapeutic drugs has been widely recognized, in many cases processes and methods to systematically address those issues are lacking. For example, despite numerous attempts to standardize guidelines for determination of neutralizing and non-neutralizing ADAs (Mire-Sluis, A. R. et al. 2004 J. Immunol. Methods. 289: 1-16; Shankar, G. et al. 2008 J. Pharm. Biomed. Anal. 48: 1267-1281; Gupta, S. et al. 2007 J. Immunol. Methods 321: 1-18; Gupta, S. et al. 2011 J. Pharm. Biomed. Anal. 55: 878-888; Koren, E. at al. 2008 J. Immunol. Methods 333: 1-9; Shankar, G. et al. 2014 AAPS J. 16: 658-673; Barbosa, M. D. F. S. et al. 2012 J. Immunol. Methods 384:152-156; all expressly incorporated by reference herein), methods used to test ADAs for similar therapeutic drugs have varied widely, resulting in discrepant results and/or inability to compare products regarding their immunogenicity profile (Barbosa, M. D. F. S. et al., 2012 Drug Dscov. Today 17: 1282-1288; Barbosa, M. D. F. S. and Smith, D. D. 2014 Drug Discov. Today 19: 1897-1912; all expressly incorporated by reference herein). One of the major problems is that assay formats differ from one product to the next.

The present invention provides methods and compositions for evaluation of immunogenicity risk and/or immune responses against therapeutic drugs. Such methods and processes can be used to stratify patients prior to therapy, and/or to monitor efficacy and/or safety of therapy, and/or to guide discovery of novel therapeutic entities, and/or to guide therapeutic drug development, and/or to estimate possibility of adverse events, and/or to compare therapeutic drugs, and/or to estimate need for tolerance induction, and/or to empower doctors and patients regarding treatment decisions, and/or for postmarketing surveillance.

BRIEF SUMMARY OF THE INVENTION

This invention is directed to compositions and methods to evaluate safety and/or efficacy of therapeutic drugs for several applications, and/or to compare drugs used for treatment of the same diseases. In various aspects, the detection of anti-drug antibodies (ADAs) can be used and also combined with information compiled and analyzed in anonymized databases.

In one aspect, portable devices for ADA testing can be used by patients (self-test), at a point of care such as a physician's office, or in clinical trials, to detect antibodies against specific therapeutic drugs. In another aspect, the portable device can be used to test antibodies against a therapeutic drug in patients or animals, prior and/or after exposure to said drug. In a further aspect, any assay that detects ADAs can be used to generate data that is compiled in the database and/or used to validate the portable device. The therapeutic drug can be either a chemical entity, or a therapeutic-protein (for example insulin or enzyme replacement therapies), or another molecular entity, including but not restricted to antibodies and a combination of chemical entity and protein drug. Gene therapy is also within the scope of this application. In a further aspect, the portable ADA detection device can be used as a companion diagnostic.

In another aspect, the portable device for ADA detection contains an access code for a database. The information in the database can include, but is not restricted to MEW class II haplotypes of patients (anonymized data) and/or animals, protein epitopes related to immunogenicity or tolerance, other genetic components, analyses of associations between protein epitopes and/or patient genetics and ADA incidence.

In a further aspect, the databases can contain information related to specific therapeutic drugs and gene therapy, which could be obtained from preclinical, clinical or postmarketing studies. That information can also be compiled from the scientific literature and other sources. Data can be subject to statistical analysis and can also be used to guide drug discovery and/or development.

In another variation, the database contains information that can aid patients, physicians, or other users regarding comparing therapies and therapy selection. The information in the database can be used in conjunction with the data from the portable ADA testing device.

The present invention provides methods that can be used for various applications, including but not restricted to the following: selection of therapeutic drug for patient treatment; evaluation of the need to change therapeutic drug or to apply tolerance regimens; selection of patients for clinical trials; comparison of therapeutic drugs marketed for a given disease; scientific guidance for drug discovery and/or development; postmarketing surveillance.

BRIEF DESCRIPTION OF THE DRAWINGS

FIG. 3. Non-limiting example of a section of a database of beta interferons (IFN-β), which are used for treatment of relapsing-remitting multiple sclerosis. The front views can provide links to additional information. [a]Compiled from product labels and other clinical studies. [b]Obtained in studies using an ADA testing device of the present invention. [c]Lowest and highest reported ADA incidence; direct comparison between drugs may not be accurate due to different assays used for the tests, differences in sample collection and management and other confounding factors. The front views can provide links to additional information. NA, not applicable; ND, not determined; ADA, anti-drug antibody; PDAD, data obtained with the portable device for ADA detection; CMC, chemistry, manufacture and control.

FIG. 4. Non-limiting example of a section of a database of insulins, which are used for treatment of diabetes. The front views can provide links to additional information. NA, not applicable; ND, not determined; ADA, anti-drug antibody; PDAD, data obtained with the portable device for ADA detection; CMC, chemistry, manufacture and control.

DETAILED DESCRIPTION OF THE INVENTION

Figure 1:
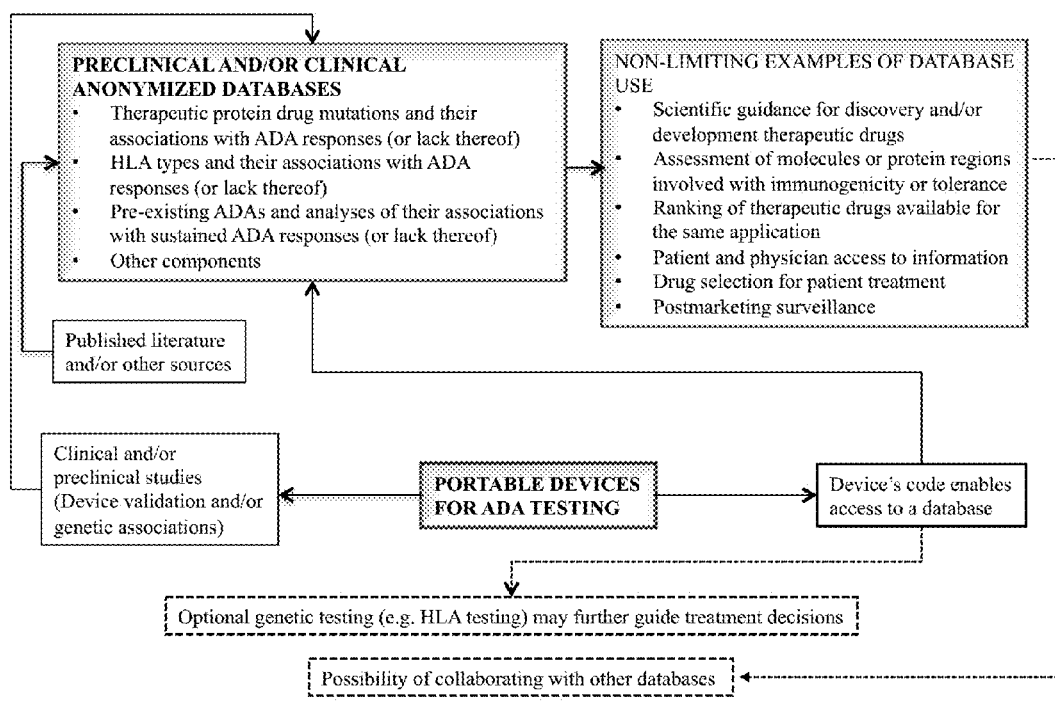
FIG. 1. Schematic representation of integrated components of the current invention. Databases may comprise (but are not restricted to) genetic associations (or lack thereof) with anti-drug antibodies (ADAs), ADA data, patient and physician forums, and literature resources. Other components discovered to be in association (or lack thereof) with anti-drug antibodies (ADAs) are also incorporated. Clinical and/or pre-clinical evaluation of portable devices used to detect ADAs can be one of the sources of the sources of data. In addition, various methods can be used to detect ADAs, including but not restricted to assays used in studies designed to validate the portable devices of the present invention. The database can be assembled using data from one or more sources, such as new data obtained in clinical studies, new data from pre-clinical studies, data available in published literature and other sources.

The present invention includes methods and compositions to anticipate and detect host immune reactions against therapeutic drugs, and to perform risk assessment for those therapeutic entities. Devices enabling, but not restricted to, self-testing and/or testing at a point of care such as at physician's office, hospital or emergency room, can be used to detect antibodies against therapeutic drugs. That information regarding the presence or absence of antibodies against the drug can be used independently or combined. In various aspects, anonymized information derived from clinical and/or pre-clinical studies and found in association (or lack thereof) with host immune responses against therapeutic drugs are organized in databases. The information and analysis results in each database can be used independently or can be combined with other tools.

In order that the invention may be more completely understood, and also to incorporate efforts at standardizing the nomenclature used in connection with therapeutic drugs, several definitions are set forth below. Such definitions are meant to encompass grammatical equivalents.

By "immunogenicity" as used herein is meant the ability of a protein or another substance or molecule to elicit a host's immune response.

By "tolerance" as used herein is meant immune tolerance to a protein or another substance or molecule, typically characterized by the lack of immune responses.

By "antibody" as used herein is meant a protein that binds an amino acid sequence or another molecular entity. In mammals such as humans and mice, antibodies contain paired heavy and light polypeptide chains. Each chain contains a variable and a constant region. The variable regions of the light and heavy chains are required for binding the target antigen.

By 'ADA" or "anti-drug antibody" as used herein is meant antibody that bind to a protein or other molecular-entity or target antigen, whereas that protein or other molecular entity or antigen can be a therapeutic drug. In that sense, all antibodies are essentially "binding".

By "NAb" or "neutralizing antibody" as used herein is generally meant antibody that "inhibits or reduces the pharmacological activity of the biologic drug molecule, as determined by an in vitro test or animal-based bioassay method, regardless of its in vivo clinical relevance (i.e., whether or not test method results relate to clinical impact in the subject)"; (Shankar, G. et al. 2014 AAPS J. 16: 658-673; expressly incorporated by reference herein). Furthermore, within the general scope of this definition, the term "NAb" can be used for an antibody directed against any other molecular entity or target antigen.

By "antigen" as used herein is meant a substance that induces an immune response.

By "target antigen" as used herein is meant the molecule that is bound specifically by the variable region of a given antibody. A target antigen may be a protein, carbohydrate, lipid, or other chemical compound.

By "antibody epitope" as used herein is meant the region of the target antigen that binds to the antibody variable region.

By "immunoglobulin (Ig)" herein is meant a protein consisting of one or more polypeptides substantially encoded by immunoglobulin genes. Immunoglobulins may have a number of structural forms, including but not limited to full length antibodies, antibody fragments, and individual immunoglobulin domains. Immunoglobulins include but are not limited to antibodies.

By "isotype" as used herein in regards to antibodies, is meant any of the subclasses of immunoglobulins defined by the chemical and antigenic characteristics of their constant regions. The currently known human immunoglobulin isotypes are IgG1, IgG2, IgG3, IgG4, IgA1, IgA2, IgM1, IgM2, IgD, and IgE.

By "IgG" as used herein is meant a polypeptide belonging to the class of antibodies that are substantially encoded by a recognized immunoglobulin gamma gene. In humans this class comprises IgG1, IgG2, IgG3, and IgG4. Also included are hybrids of IgG proteins in which amino acids for one IgG protein substituted for amino acids of a different IgG protein (e.g. IgG1/IgG2 hybrids).

By "amino acid" as used herein is meant one of the 20 naturally occurring amino acids or any non-natural analogues that may be present at a specific, defined position.

By "protein" herein is meant attached amino acids. The protein may be made up of naturally occurring amino acids and peptide bonds, or synthetic peptidomimetic structures, i.e. "analogs", such as peptoids (see Simon, R. J. et al. 1992 Proc. Natl. Acad. Sci. USA 89: 9367-9371). Thus "amino acid", or "peptide residue", as used herein encompasses both naturally occurring and synthetic amino acids.

By "database" as used herein is meant a structured combination of information and/or data analyses, which can be accessed in one or more ways.

By "assay" as used herein is meant a procedure for testing samples.

By "ADA portable device" as used herein is meant a portable device of the present invention, which allow for testing samples regarding the presence of ADA.

By "chemistry, manufacturing and control (CMC)" factors as used herein is meant product quality factors such as impurities, contaminants, aggregates and other product-related degradants, factors resulting from the recombinant expression system used for proteins (such as nonhuman glycosylation), factors resulting of the protein design (for example, change in aggregation patter as a result of PEGylation).

By "PEGylation" as used herein is meant the addition of one or more polyethylene glycol (PEG) moiety by various means that may comprise the use of linkers.

By "target cell" as used herein is meant a cell that expresses a target antigen.

By "variant protein", "protein variant", "variant polypeptide", or "polypeptide variant" as used herein is meant a polypeptide sequence that differs from that of a parent polypeptide sequence by virtue of at least one amino acid modification. Variant polypeptide may refer to the polypeptide itself, a composition comprising the polypeptide, or the amino sequence that encodes it.

By "full length antibody" as used herein is meant the structure that constitutes the natural biological form of an antibody, including variable and constant regions, including one or more modifications. Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each. In certain variations, antibody may mean a protein consisting of one or more polypeptides substantially encoded by all or part of the recognized immunoglobulin genes. Antibody herein is meant to include full length antibodies and antibody fragments, and may refer to a natural antibody from any organism, an engineered antibody, or an antibody generated by recombinant techniques for experimental, therapeutic, or other purposes.

By "labeled Antibodies" as used herein is meant antibodies that have the addition of one or more labels. For example, gold-labeled anti-host antibodies can be used to detect antigen-antibody complexes (Hsu, Y. H. 1984 Anal. Biochem. 142: 221-225; expressly incorporated by reference herein).

In another embodiment, proteins and/or other molecules can be labeled and used for generation of assay signal (Lou, S. C. et al. 1993 Clin. Chem. 39: 619-624; expressly incorporated by reference herein). In some embodiments, labels can be used in various forms to generate a detectable signal. The assay readout can be either the signal generated or inhibition of signal.

The term "labelling group" as used herein means any detectable label. In some embodiments, the labelling group is coupled to the antibody via spacer arms of various lengths to reduce potential steric hindrance. Various methods for labelling proteins are known in the art and may be used in performing the present invention. In general, currently known labels fall into a variety of classes, depending on the assay in which they are to be detected. For example: a) isotopic labels, which may be radioactive; b) magnetic labels; c) redox active moieties; d) optical dyes; e) enzymatic groups such as horseradish peroxidase, beta.-galactosidase, luciferase, alkaline phosphatase; f) biotinylated groups. Various methods for labelling proteins are known in the art and may be used in performing the present invention.

Specific labels can include but are not limited to optical dyes, including, but not limited to, chromophores, phosphors and fluorophores. Fluorophores can be either "small molecule" (chemical entity) or protein, or a combination.

By "fluorescent label" is meant any molecule that may be detected based on its fluorescent properties. Suitable fluorescent labels include, but are not limited to fluorescein, rhodamine, tetramethylrhodamine, eosin, erythrosin, malacite green, stilbene, Lucifer Yellow, Cascade Blue®, Cascade Yellow, Texas Red®, IAEDANS, EDANS, BODIPY® FL, LC Red 640, Cy®5, Cyanine5.5, LC Red 705, Oregon Green® 488, Alexa-Fluor® dyes, R-phycoerythrin, fluorescein isothiocyanate (FITC), Texas Red®. Other appropriate optical dyes can also be used.

Appropriate proteinaceous labels also include, but are not limited to, green fluorescent protein (GFP) including from *Renilla, Ptilosarcus*, or *Aequorea* species, blue fluorescent protein, yellow fluorescent protein, luciferase, and beta galactosidase (Cormier, M. J. and Eckroade, C. B. 1962 Biochim. Biophys. Acta 64: 340-344; Krasitskaya, V. V. 2011 Ana. Bional. Chem. 401: 2573-2579; Chalfie, M. et al. 1994 Science 263: 802-805; Heim, R. et al., 1996 Curr. Biol. 6:178-182; Leuvering, J. H. W. 1980 J. Immunoassay Immunochem. 1: 77-91; Nolan, G. P. et al. 1988 Proc. Natl. Acad. Sci. U.S.A. 85: 2603-2607; Tsien, R. Y. 1998 Annu. Rev. Biochem. 67: 509-544 Prasher, D. C. et al. 1992 Gene 15:229-233; Stauber, R. H. 1998 Biotechniques 24:462-471; all expressly incorporated by reference herein).

Colloidal-gold, silver enhanced gold, blue latex bead and carbon black nanoparticles are labels known in the art that can also be utilized for the present invention (Linares, E. M. et al., 2012 J. Immunol. Methods 375:264-270; Choi, D. H. et al. 2010 Biosensors and Bioelectronics 25: 1999-2002; Yokenita, T. et al. 2013 J. Microbiol. Methods 93: 251-256; all expressly incorporated by reference herein). Other labels capable of generating a suitable signal can also be used.

In another embodiment, novel labels discovered by any techniques, including but not restricted to genetic analysis of different species, or by any chemical, biochemical or other means, can be incorporated in assays used in the present invention, and are within the scope of its utility.

Detection of Anti-Drug Antibodies (ADAs):

The present invention includes but is not restricted to methods for detection of ADAs in body fluids (including but not restricted to blood and serum) and tissue samples. In another embodiment, antibodies bound to cells and/or various matrices can be detected. The described methods are not meant to constrain the present invention to any particular application or theory of operation. Rather, the provided methods are meant to illustrate generally that one or more techniques can be used to detect ADA against therapeutic drugs. Furthermore, in one embodiment an application is described that provides a means of utilizing a method to detect ADAs for individual testing and/or with portable devices. Validation of the portable devices may include using them for tests with clinical samples, and comparison with other assays known in the art.

Assays may employ a variety of detection methods including but not limited to chromogenic, fluorescent, luminescent, or isotopic labels. Binding assays can be carried out using a variety of methods known in the art, for example including but not limited to surface plasmon resonance (SPR), FRET (Fluorescence Resonance Energy Transfer) and BRET (Bioluminescence Resonance Energy Transfer)-based assays, AlphaScreen® (Amplified Luminescent Proximity Homogeneous Assay), Scintillation Proximity Assay, ELISA (Enzyme-Linked Immunosorbent Assay), gel electrophoresis, chromatography, immunoprecipitation, and radioimmunoassays (Assa, S. and Benjamini, Y. 1993 Br. J. Biomed. Sci. 50: 103-108; Barbosa, M. D. F. S. et al. 2006 Clin. Immunol. 118: 42-50; Barbosa, M. D. F. S. 2012 J. Immunol. Methods 384: 152-156; Barbosa, M. D. F. S. et al. 2013 Anal. Biochem. 441: 174-179; Berson, S. A. and Yalow, R. S. 1957 Diabetes 6: 402-405; Berson, S. A. and Yalow, R. S. 1957 J. Clin. Invest. 36: 642-647; Berson, S. A. and Yalow, R. S. 1958 Am. J. Med. 25: 155-159; Berson, S. A. and Yalow, R. S. 1996 Obes. Res. 4: 583-600; Bray, G. L. et al. 1993 Am. J. Hematol. 42: 375-379; Dai, S. et al. 2014 AAPS J. 16: 464-477; Li, J. et al. 2011 J. Pharm. Biomed. Anal. 54: 286-294; Gong, H. and Urlacher, T. 2015 Anal. Biochem. 469: 1-3; Lofgren, J. A. et al. 2007 J. Immunol. 178: 7467-7472; Mire-Sluis, A. R. et al. 2004 J. Immunol. Methods 289: 1-16; Ritter, G. et al. 2001 Cancer Res. 61: 6851-6859; Tatarewicz, S. M. et al. 2012 J. Immunol. Methods 382: 93-100). All of the above-cited references are expressly incorporated herein by reference.

In one embodiment, the portable ADA testing device of the present invention may detect selected ADA isotypes. In another embodiment, the ADA assays of the present invention may comprise modifications to allow detection of all antibody isotypes. In another embodiment, the assays may also allow identification of the isotype species in the sample. The testing devices may be tailored to detect individual samples or multiple samples. In another embodiment, the portable device may be used for antibody epitope mapping.

By "lateral flow" or "lateral flow technology" or "lateral flow assay" as used herein is meant a technology or assay based on the principle that the test substance and/or reagents flow in one (or more than one) direction, and may result in detection of a test substance (Ahn, J. S. et al. 2003 Clin. Chim. Acta 332:51-59; Chan, C. P. et al. 2003 J. Immunol. Methods 279: 91-100; Choi, D. H. et al. 2010 Biosens. Bioelectron. 25: 1999-2002; Chowdry, V. K. 2014 J. Virol. Methods 197: 14-18; Choi, S. et al. 2004 Clin. Chim. Acta 339: 147-156; Corstjens, P. 2011 Clin. Biochem. 44: 1241-1246; Corstjens, P. L. et al. 2016 Clin. Biochem. 49: 22-31; Geertruida, A. et al. 2009 Anal. Bioanal. Chem. 393: 569-582; Koizumi, D. et al. 2014 Food Chem. 150: 348-352; Laderman, E. I. et al. 2008 Clin. Vaccine Immunol. 15: 159-163; Linares, E. M. et al. 2012. J. Immunol. Methods 375:264-270; Lu, S. Y. 2012 Anal. Biochem. 422: 59-65; Nabatiyan, A. et al. 2010 J. Acquir. Immune Defic. Syndr. 53: 55-61; Nielsen, K. 2008 J. Immunoassay Immunochem. 29: 10-18; Nielsen, K. et al. 2009 J. Immunoassay Immunochem. 30: 313-321; Oem, J. K. 2009 Clin. Vaccine immunol. 16: 1660-1664; Offermann, N. 2014 J. Immunol. Methods 403: 1-6; Oh, Y. K. 2014 Biosens. Bioelectron. 61: 285-289; Peng, T. 2014 J. Food Prot. 10: 1824-1829; Rundstrom, G. 2007 Clin. Chem. 53: 342-348; Song, X. and Knotts, M. 2008 Anal. Chim. Acta 626: 186-192; Teerinen, T. 2014 Anal. Bioanal. Chem. 406: 5955-5965; van Dam. G. J. et al. 2013 Exp. Parasitol. 135: 274-282; Wilkinson, R. et al. 2003 Ann. N Y Acad. Sci. 990: 386-390; Yonekita, T. et al. 2013 J. Microbiol. Methods 93: 251-256; all expressly incorporated by reference herein). In another embodiment, vertical flow can be used. In another embodiment, the reactions of the portable ADA testing device can be performed without flow of reagents, samples or test substances.

None of the prior art utilizing lateral flow technology has identified the unifying methods, devices and approach disclosed in embodiments of the present invention, for standardization of ADA measurements in the broad context of immunogenicity of therapeutic drugs. This is despite the fact that prior art on general principles of lateral flow technology dates of at least as early as 1971 (U.S. Pat. No. 3,620,677, which is incorporated herein by reference in its entirety). Additional non-limiting examples of patents disclosing lateral flow technology include the following US Patent Numbers, all incorporated by reference in their entirety herein: U.S. Pat. Nos. 3,811,840; 3,888,629; 4,042,335; 4,168,146; 4,169,138; 4,258,001; 4,313,734; 4,235,601; 4,366,241;

4,348,207; 4,446,232; 4,435,504; 4,459,358; 4,503,143; 4,537,861; 4,594,327; 4,624,929; 4,703,017; 4,632,901; 4,756,828; 4,999,285; 4,654,309; 4,623,461; 4,806,311; 4,861,711; 4,868,108; 4,770,853; 4,803,170; 4,960,691; 5,030,558; 4,857,453; 4,855,240; 4,920,046; 4,963,468; 4,981,786; 5,006,474; 4,916,056; 4,956,302; 5,039,607; 5,079,174; 5,120,504; 5,075,078; 5,164,294; 5,141,850; 5,248,619; 5,356,782; 5,939,331; 6,485,982; 9,377,458.

Modifications to increase sensitivity and accuracy of the assays may include but are not restricted to, for example, optimization of the detection method and of sample collection and size, minimization of nonspecific background signal, matrix optimization, selection of time for assay development and signal reading. In another embodiment, modifications are made to improve biophysical properties of the regents used for the assay, including but not limited to stability, solubility, and oligomeric state.

Data-Driven Databases of Factors Associated with Efficacy and Safety of Therapeutic Drugs:

In one embodiment, the databases will be organized to enable data-driven estimation of therapeutic drug safety, as it relates to the presence of ADAs. In another embodiment, the databases can enable data-driven estimation of drug efficacy for patient populations, based on the incidence on NAbs. Those drugs may comprise but are not limited to therapeutic proteins (biotherapeutics), or natural products, or small molecule drugs, or peptides, or small-molecule-biotherapeutic conjugates, or a combination of those therapeutic drugs. In another embodiment, the database allows comparison of different therapeutic drugs used for the same application.

In another embodiment, the therapeutic drug can be, but is not restricted to, an enzyme replacement therapy, an immunemodulator, an antibody, a therapeutic vaccine, or an antimicrobial agent.

In another embodiment, the therapeutic drug is a biosimilar (Barbosa, M. D. F. S. and Smith, D. D. 2014. Drug Discov. Today 19: 1897-1912; expressly incorporated by reference herein). By "biosimilar' as used herein is meant a therapeutic protein (biotherapeutic) similar to another one already marketed for which the patent has expired (the "reference product").

In another embodiment, the therapeutic drug is a biobetter (Barbosa, M. D. F. S. and Smith, D. D. 2014 Drug Discov. Today 19: 1897-1912; expressly incorporated by reference herein). By "biobetter" as used herein is meant a newer version of a marketed biotherapeutic.

In an alternate embodiment, the databases and methods of the present invention are used to associate genetic components with risk of adverse events or likelihood of low drug efficacy. By "adverse event" as used herein is meant any undesirable experience (i.e., a bad side effect) associated with the use of a product. In another embodiment, the information organized within databases, used alone or in combination with additional individual testing, can be used to evaluate postmarketing drug efficacy or safety. By "postmarketing" as used herein is meant after a therapeutic drug has received approval from a regulatory agency, for example the U.S. Food and Drug Administration (FDA) or the European Medicines Agency (EMA). In another embodiment, those postmarketing comparisons may also aid ranking of drugs approved for the same indication, including but not restricted to biosimilars and biobetters (Barbosa, M. D. F. S. 2011 Drug Discov. Today 16: 345-353; Barbosa, M. D. F. S. et al. 2012 Drug Discov. Today. 17: 1282-1288; Barbosa, M. D. F. S. and Smith, D. D. 2014 Drug Discov. Today 19: 1897-1912; all expressly incorporated by reference herein).

In another embodiment, the ADA-testing devices of the present invention contain information allowing access to the database. Various levels of security and access can applied to the database. For example, a device that that tests for ADAs against insulin may also contain a code allowing access to a section of the database that contains data pertaining to evaluation of efficacy or safety of insulin products, without allowing access for example to a section of the database that contains data pertaining to interferon-β. Those security levels and access can be changed if deemed appropriated. These examples are meant to illustrate the versatility of the databases, without constraining their use or construction.

The ADA-testing devices of the present invention may be compared with one or more conventional assay used for a given drug, such as for example a radioimmunoassay to test for antibodies against insulin or another assay relevant for comparisons (Berson, S. A. and Yalow, R. S. 1957 Diabetes 6: 402-405; Berson, S. A. and Yalow, R. S. 1957 J. Clin. Invest. 36: 642-647; Berson, S. A. and Yalow, R. S. 1958 Am. J. Med. 25: 155-159; Berson, S. A. and Yalow, R. S. 1996 Obes. Res. 4: 583-600; Hamasaki, H. and Yanai, H. 2014 Diabetes Metab. 40: 481-482; all expressly incorporated by reference herein). The parameters tested may include but are not limited to factors such as sensitivity, robustness, inter and intra assay variation, precision, sensitivity, matrix interference, cut point determination, minimal required dilution, and drug inhibition of the assay (Barbosa, M. D. F. S. et al. 2006 Clin. Immunol. 118: 42-50; Barbosa, M. D. F. S. et al. 2012 J. Immunol. Methods 384:152-156; Mire-Sluis, A. R. et al. 2004 J. Immunol. Methods 289:1-16; Shankar, G. et al 2008 J. Pharm. Biomed. Anal. 48: 1267-1281; all expressly incorporated by reference herein).

The ADA-testing devices of the present invention may be further validated in clinical and/or preclinical studies. That validation may include but not be restricted to comparison of data obtained with samples from the same humans or animal models, tested with an ADA-testing device of the present invention and another assay known in the art or newly invented. Data obtained from those studies can be submitted to analysis and incorporated into databases of the present invention. Other forms of ADA-testing device validation may also be used.

The ADA-testing devices of the present invention can be used alone to provide information of the ADA positive or negative status or can be is used in conjunction with a database and with statistical analyses to infer the probability of safety or efficacy issues due to ADA responses.

In another embodiment, the databases and methods of the present invention are used to assess risk of immune reactions other than anti-drug antibodies. Those reactions may include but are not restricted to various types of hypersensitivity (Barbosa, M. D. F. S. and Smith, D. D. 2014 Drug Disc. Today. 12: 1897-1912; expressly incorporated by reference herein).

In another embodiment, factors other than human genetics that may affect protein immunogenicity are investigated and used for association analyses, including but not limited to amino acid sequence of the protein, glycosylation, deamidation, aggregation, impurities, and subvisible particles (Barbosa, M. D. F. S. and Celis, E. 2007 Drug Discov. Today 12: 674-681; Barbosa, M. D. F. S. 2011 Drug Discov. Today 16: 345-353; Barbosa, M. D. F. S. et al. 2012 Drug Discov. Today 17: 1282-1288; Chirino, A. J. and Mire-Sluis, A. 2004

Nat. Biotechnol. 22: 1383-1391; all expressly incorporated by reference herein). For example, switching from insulin glargine to insulin degludec reduced anti-insulin antibody in antibody-positive subjects with type 1 diabetes and the observed immune responses might be due to protein misfolding ((Hamasaki, H. and Yanai, H. 2014 Diabetes Metab. 40: 481-482; Monnier, L. et al. 2014 Diabetes Metab. 40: 483-484; all expressly incorporated by reference herein). Another example is the different formulations of interferon-β that are used for the treatment of multiple sclerosis, each eliciting ADA responses in a different percentage of patients, which might be linked to differential aggregation of the drugs (Barbosa, M. D. F. S. et al. 2006. Clin. Immunol. 118: 42-50; Barbosa, M. D. F. S. et al. 2012. Drug Discov. Today. 17: 1282-1288; Barbosa, M. D. F. S. and Smith, D. D. 2014. Drug Discov. Today 19: 1897-1912; Runkel, L. et al. 1998. Pharm. Res. 15:641-649; all incorporated by reference herein).

Currently no mechanisms are in place to systematically test patients for antibodies against marketed drugs and to comparatively evaluate postmarketing drug efficacy (Barbosa, M. D. F. S. and Smith, D. D. 2014 Drug Discov. Today 19: 1897-1912; expressly incorporated by reference herein). This can result in patients receiving medications that are very unlikely to provide any benefit, because neither the patient nor the physician knows or suspects that the patient carry or is likely to develop neutralizing antibodies (NAbs) against the drug in question. For example, in a postmarketing clinical study designed to investigate associations between patient genetics and IgG responses against interferon-β (IFN-β), it was observed that some of the patients had very high levels of anti IFN-β IgG; ADA neutralizing activity was observed for plasma samples of those patients even when tested with a low sensitivity cell-based assay (see Barbosa, M. D. F. S. et al. 2006. Clin. Immunol. 118: 42-50, which includes an Appendix A. Supplementary data; expressly incorporated by reference herein). Due to the requirement to anonymize the samples and data in that postmarketing study (samples were obtained through SeraCare Life Sciences Inc.), it was not possible to inform the physicians and patients of the high antibody levels that could be negatively affecting the therapy, so that an alternative therapy would be considered. Using the ADA portable devices of the present invention, it can be possible for the patients and/or physicians to perform ADA tests that could guide therapy. Furthermore, it would allow the patients and doctors to have access to information that includes but is not restricted to anonymized genetic data and genetic associations with ADA. Hence, even in cases when the test result for ADA is negative, it is possible to estimate the likelihood of an ADA response ensuing during the course of therapy, based on the patient genetics. The portable device can make the ADA information readily available to patient at home or at point of care such as a physician's office, aiding therapeutic drug selection for use, and leading to corrective measures or the evaluation of the need to switch to another therapy. In cases when an alternative therapy is not an option (for example, for some currently used enzyme replacement therapies), the information obtained with the ADA testing devices and corresponding databases can guide the need for tolerance induction regimens (Banugaria, S. G. et al. 2001 Genet. Med. 13: 729-736; Byrne, B. J. et al. 2011 Mol. Genet. Metab. 103: 1-11; Messinger, Y. H. et al. 2012 Genet. Med. 14:135-142; Wang, J. et al. 2008 Nat. Biotechnol. 26:901-908; all expressly incorporated by reference herein).

By "megadata" ("big data") as used herein is meant a large volume of patient records derived from physician-supervised treatment and insurance company claims (Barbosa, M. D. F. S. and Smith, D. D. 2014 Drug Discov. Today. 19: 1897-1912; expressly incorporated by reference herein). The databases and devices of the present invention can be used in connection with megadata analysis, including but not restricted to allow comparison of therapeutic drugs and gene therapy.

By "distributed analysis" as used herein is meant "an analysis that is distributed across multiple computers simultaneously; following the parallel computations, the results are combined centrally" (Barbosa, M. D. F. S. and Smith, D. D. 2014 Drug Discov. Today 19: 1897-1912; expressly incorporated by reference herein). In another embodiment, distributed analysis may be used when building, updating or consulting the database of the present invention.

In another embodiment, the ADA testing devices of the present invention can be used to guide selection of therapeutic drug dose. Therapeutic drug dose selection for humans is typically made during phase 1 clinical trials, using a limited number of human subjects. Pre-existing antibodies or ADAs that develops during the course of therapy can be an additional difficulty for selection of the correct dose of the corresponding therapeutic drug. When the ADAs are neutralizing, they can abolish drug efficacy, and higher drug concentrations may be required to counteract the ADA effects.

In another embodiment, the ADA testing device of the present invention and corresponding database can be used to select patients for clinical trials, including but not restricted to clinical development of novel biotherapeutics, biosimilars or biobetters.

By "pre-existing antibody" as used herein, is meant an antibody against a therapeutic drug or other molecular entity that was present in the body of a human or animal prior to exposure to or administration of that therapeutic drug. In another embodiment, the device of the present invention can be used to test pre-existing antibodies in humans or animals. Data collected may be used for statistical analyses to investigate correlations.

Pre-existing antibodies may be indicative of therapeutic drug efficacy or safety. For example, pre-existing anti-infliximab antibodies in inflammatory bowel disease patients were predictive of safety and efficacy of treatment of those patients with infliximab (Steenholdt, C. 2013 Dan. Med. J. 60: B4616; Steenholdt, C. 2013 Aliment. Pharmacol. Ther. 37: 1172-1183; Steenholdt, C. 2013 Ther. Drug Monit. 35: 530-538; all expressly incorporated by reference herein). In another example, the presence of IgE specific for galactose-alpha-1,3-galactose can be predictive of cetuximab-induced anaphylaxis (Chung, C. H. et al. 2008 N. Engl. J. Med. 358: 1109-1117; expressly incorporated by reference herein).

Animal Models:

The therapeutic drug data to be incorporated in the database(s) of the present invention may be obtained from experiments in humans and/or animal models, and/or cells, and/or tissues, and/or other organism. As is known in the art, drugs are often tested in animals, including but not limited to mice, rats, rabbits, dogs, cats, pigs, and monkeys, in order to measure a drug's efficacy for treatment against a disease or disease model, or for testing the drug's pharmacokinetics, toxicity, and other studies. The animals may be referred to as "disease models".

In another embodiments, immunogenicity of therapeutic drugs of the present invention may be assessed in a clinically relevant disease model of various human diseases. Relevant models may include transgenic animals.

Clinical Use of ADA-Testing Devices and Related Databases:

The databases and assays of the present invention may be used within various therapeutic areas and animal disease models. Therapeutic areas in which this invention can be applied include but are not restricted to diabetes, cancer, inflammation, neurological diseases, cardiovascular disease, autoimmune diseases, antimicrobials, multiple sclerosis, and numerous rare diseases. From the foregoing and subsequent descriptions, one skilled in the art can easily adapt the ideas, methods and compositions of the current invention for other therapeutic areas and newly described diseases. Therefore, such embodiments are included in the scope and claims of this invention.

A "patient" for the purposes of the present invention includes both human and other animals, preferably mammals and most preferably humans.

The term "treatment" in the present invention is meant to include therapeutic treatment, as well as prophylactic, or suppressive measures for a disease or disorder. "Treatment" also encompasses administration of a therapeutic drug after the appearance of the disease in order to ameliorate, control, or to eradicate the disease. Those "in need of treatment" include mammals already having the disease or disorder, as well as those prone to having the disease or disorder, including those in which the disease or disorder is to be prevented.

A variety of therapeutic drugs may be used for treatment of patients in diverse combinations, such use being described herein as "combination therapy". For example, radiation and/or chemotherapy can be combined with a biotherapeutic anti-cancer drug, administered according to protocols commonly employed and known to the skilled artisan. In one embodiment, effects of "combination therapies" are also compiled in the database. In another embodiment, an ADA testing device is tailored to identify antibodies against the components of the combination therapy.

Included in the present invention are diagnostic tests to identify patients who are likely to show a favorable clinical response to a therapeutic drug, or who are likely to exhibit a significantly better response based on their genetic makeup in conjunction with immunogenicity profiles.

Furthermore, the present invention comprises prognostic tests performed on clinical samples such as blood, tissue and/or other samples. Such information may be used to identify patients for inclusion or exclusion in clinical trials, or to inform decisions regarding appropriate dosages and treatment regimens. Such information may also be used for therapeutic drug discovery and/or to select a therapeutic drug likely to provide superior therapeutic results.

EXAMPLES

Non-limiting examples are provided below to illustrate the present invention. These examples are not meant to constrain the present invention to any particular recipe, therapeutic drug, application or theory of operation. Those skilled in the art of antibody detection, data analyses and scientific knowledge generation, database management or other relevant fields of work will appreciate that, within the overall scope and vision of the current invention, modifications can be inserted without departing from the scope of this application. Accordingly, such embodiments are intended to be included within the scope of this invention.

Example 1

Evaluation Beta Interferons (IFN-β) for the Treatment of Relapsing Remitting Multiple Sclerosis Several IFN-β drugs are currently approved for the treatment of relapsing remitting multiple sclerosis (RRMS). Anti-IFN-β NAbs can affect the efficacy of those IFN-β drugs, but currently there are no regulatory requirements for systematic postmarketing monitoring of anti-IFN-β ADAs. A limited amount of data is typically used for the regulatory approval process. In addition, it has been shown that in general, the quality of data used for approval greatly varied among applications (Downing, N. S. et al. 2014 JAMA 311: 368-377; expressly incorporated by reference herein). The decision-making process of what IFN-β to use is further complicated by the recent approval of IFN-β biosimilars and biobetters for RRMS treatment, with several similar drugs with the same mechanism of action now available (Bertolotto, A. et al. 2000 Immunopharmacology 48: 95-100; Hu, X. 2015 Br. J. Clin. Pharmacol. 79: 514-522; Jaber, A. et al. 2007 Drugs R. D. 8: 335-348; Kappos, L. et al. 2005 Neurology 65: 40-47; all expressly incorporated by reference herein). Those IFN-β formulations are administered at different doses and using different routes of administration (Barbosa, M. D. F. S. and Smith, D. D. 2014 Drug Discov. Today 19: 1897-1912; expressly incorporated by reference herein). In addition, if anti-IFN-β NAbs are present and cross react with an epitope common to all IFN-β, an increased dosage may be needed to counteract the NAb effect, or available alternative therapies (other than IFN-β) may need to be considered.

The combined use of the ADA testing device with the databases of the present invention is generally illustrated in FIG. 1. More specifically, FIG. 3 provides a non-limiting example of a section of a database that can be used to compare marketed IFN-β drugs. A user of the portable device to test for the presence of anti-IFN-β antibodies may be given a code to access that database. Alternatively, other means to access the database can be provided. Some non-limiting examples of database use are provided in the next three paragraphs.

A patient or a caregiver (e.g. a physician or a nurse or other) using the portable device of the present invention to test for ADAs may access the related database to obtain information about treatment options, to obtain information on correlations between human genetics and ADA development against specific biotherapeutics, to evaluate the presence of pre-exiting antibodies as a risk factor, to evaluate the incidence of ADAs against exiting drugs, and to obtain comprehensive links to the scientific literature and/or to clinical trials. The information may guide decisions regarding the course of treatment with marketed drugs and/or guide patient selection for clinical trials, and/or suggest relevance of additional patient testing. It can also empower patients regarding their treatment. For example, if it is determined that a patient treated with IFN-β has anti-IFN-β antibodies, and additional testing indicates that they are neutralizing, there would be a risk that ADA would be abrogating the efficacy of the drug for that specific patient. In that case, an alternative therapy option may be discussed, also taking into account the clinical symptoms. In another instance, if a newly diagnosed multiple sclerosis patient tests negative for pre-existing anti-IFN-β ADAs, that patient may be a candidate for IFN-β, and if genetic associations are present in the database, patient genetic testing can further estimate the likelihood of ADA development during the course of IFN-β therapy. In addition, the portable device can be used at intervals during the course of therapy to monitor ADA incidence. In another scenario, if a newly diagnosed patient tests positive for pre-existing anti-IFN-β ADAs, the database can be searched to investigate if that patient is at a higher risk of developing neutralizing anti-IFN-β ADAs.

Companies developing new versions of existing drugs may access the database for scientific guidance. For instance, information available in the database regarding associations (or lack thereof) between patient genetics and ADA could be used to develop new versions of marketed therapeutic drugs. In another instance, comparison of the ADA incidence for drugs with different mutations may suggest what protein modifications are more likely to increase the risk of unwanted immunogenicity. In another embodiment, protein epitopes can confer tolerance and be associated with decreased ADA incidence. Furthermore, database clinical data obtained for antibody epitope mapping could further indicate regions of the drug more likely to be immunogenic. In the course of product development, human subjects enrolled in clinical trials could be monitored with the portable device for ADA development, and the database consulted to compare ADA incidence for the new drug.

Postmarketing surveillance for therapeutic drugs could also utilize the present invention. A major challenge with postmarketing ADA detection is lack of uniformity of the different assays used, which preclude reliable comparisons between different drugs. The portable device of the present invention, when used at the physician's office, would become part of the patient records. Besides, it would be a standard assay, allowing reliable comparison between various drugs. That could also include comparisons for biosimilar drugs, which follow an expedited development pathway, and whose long-term immunogenicity potential is often expected to be evaluated postmarketing.

In FIG. 3, the first column lists IFN-β therapies currently approved for treatment of RRMS, and also therapies other than IFN-β currently available for MS treatment (for example, listed as "non IFN-β MS therapies"). By clicking on the therapy name, the user can access a link with additional information for each therapy, including but not restricted to route of administration (subcutaneous, intramuscular or intravenous), frequency of administration, dose, reported side-effects, and reported efficacy at the dose tested. Similar to the organization of the first column, by clicking on links available in other columns the user may obtain additional information. The second column lists the incidence of anti-IFN-β ADA (the lowest and highest reported ADA incidence), compiled from product labels and other clinical studies. It should be noted that, using the data from the second column, direct comparison between drugs may not be accurate due to different assays used for the tests, differences in sample collection and management and other confounding factors. A warning or other means can be used to guide the user. The third column lists the incidence of anti-IFN-β ADA obtained in studies using the ADA testing device of the present invention, which can allow direct comparison between drugs. The fourth and fifth columns provide associations (or lack thereof) between MEW class II haplotypes and anti-IFN-β ADAs, data compiled from the available literature or from studies with the portable device, respectively. For example, by clicking on "DRB1*0701" on the fourth column, the user would have access to additional information, including the literature source (Barbosa, M. D. F. S. et al. 2006 Clinical Immunol. 118: 42-50; expressly incorporated by reference herein). The sixth column provides information about the molecular entities, including but not restricted to any protein engineering that may lead to changes in the biophysical properties. The seventh columns lists relevant "chemistry, manufacturing and control" (CMC) factors. For example, by clicking on the word "aggregation" in the seventh column, the user of the database could access additional information for Betaseron®, including but not restricted to published literature on its aggregation propensity and on causal relationships between aggregation and ADA responses (Barbosa, M. D. F. S. et al. 2012 Drug Discov. Today 17: 1282-1288; Runkel, L. 1998 Pharm. Res. 15: 641-649; all expressly incorporated by reference herein).

Example 2

Evaluation of Insulins for Treatment of Type 1 Diabetes

Insulin (a protein hormone secreted by pancreatic islets beta cells) consists of two polypeptide chains. Proinsulin is specifically cleaved by proteases to generate chains A and B. Insulin contains chains A and B linked together by disulfide bonds. Type 1 diabetes mellitus is characterized by lack of insulin production due to injury of the beta cells of the pancreatic islets, and therefore those patients are dependent on exogenous insulin to sustain life (Harvey, R. A. et al. 2014 Diabetes Technol. Ther. 16: 348-357; Nakayama, M. et al. 2005 Nature 435:220-223; Prasad, S. et al. 2012 J. Autoimmun. 39: 347-353; all expressly incorporated by reference herein). Many insulin formulations are currently approved for the treatment of type 1 diabetes (Arya, A. and Al-Waili, N. 2012 J. Clin. Med. Res. 4: 292-294; Becker, D. I. 2002 Diabetes Care 25: 1663; Edwards, K. L. et al. 2010 Pharmacotherapy 30: 955-965; Garg, S. K. et al. 1999 Diabet. Med. 16: 384-387; Johnson, N. B. et al. 1992 Diabetes Care 15: 1031-1033; all expressly incorporated by reference herein). In addition, the patents for some of insulin drugs have expired, and biosimilars and biobetters are being developed. Anti-insulin NAbs may affect the efficacy of that drug, but currently there are no regulatory requirements for systematic postmarketing monitoring of anti-insulin ADAs (Palmer, J. P. et al. 1983 Science 222: 1337-1339; expressly incorporated by reference herein). Further to the above issues, it has been shown that in general the quality of data used for therapeutic drug approval greatly varied among applications (Downing, N. S. et al. 2014 JAMA 311: 368-377; expressly incorporated by reference herein). It is noted that if anti-insulin NAbs are present and cross react with an epitope common to all approved insulin formulations, an increased dosage may be needed to counteract the NAb effect, or tolerance regimens might need to be considered (Messinger, V. H. et al. 2012 Genet. Med. 14:135-142; expressly incorporated by reference herein).

The combined used of the ADA testing devices with the databases of the present invention is generally illustrated in FIG. 1. More specifically, FIG. 4 provides a non-limiting example of a section of a database that can be used to compare marketed insulin drugs. A patient or caregiver (e.g., a physician, or nurse, or other) using the portable devices of the present invention to test for the presence of anti-insulin antibodies can be given a code to access the corresponding databases. Alternatively, other means to access the database can be provided. Some non-limiting examples of database use are available in the next three paragraphs.

A patient or a caregiver (e.g. a physician, or a nurse, or other) using the portable device of the present invention to test for ADAs may access the related database to obtain information about treatment options, to obtain information on correlations between human genetics and ADA development against specific biotherapeutics, to evaluate the presence of pre-exiting antibodies as a risk factor, to evaluate the incidence of ADAs against exiting drugs, and/or to obtain comprehensive links to the scientific literature and/or to clinical trials. The information may guide decisions regarding the course of treatment with marketed drugs and/or guide patient selection for clinical trials, and/or suggest relevance of additional patient testing. For example, human anti-insulin antibodies could impact drug efficacy, and it has been shown that they can be involved in the etiology of diseases (Faulk, W. P. et al. 1971 "Human anti-insulin antibodies" J. Immunol. 106: 1112-1116; expressly incorporated by reference herein). Additional testing could be recommended to determine if the ADAs are neutralizing. ADA data may help discussions regarding tolerance inducing regimens, or dosing. For instance, if a type-1 diabetic (insulin dependent) is also a terminally ill cancer patient for whom the previously used insulin dosages have become ineffective to control blood sugar levels, a quick test with the portable ADA testing device could detect if the insulin resistance has developed as a consequence of ADA incidence. That could guide insulin dose increase in combination with blood sugar monitoring to provide that patient comfort during the terminal stages of the disease. In addition, the portable device can be used by diabetic patients at intervals during the course of insulin therapy to monitor ADA incidence. If the patient develops ADAs against a given insulin version, antibody epitope mapping with the portable device of the present invention may indicate if there is a mutated region in the insulin used that could be triggering the immune response. If such is the case, switching to a different insulin version might be an option. In yet another scenario, if a newly diagnosed patient tests positive for pre-existing anti-insulin ADAs, the database may be searched to investigate if that patient is at a higher risk of developing neutralizing ADAs.

Companies developing new versions of existing drugs may access the database for scientific guidance. For instance, information available in the database regarding statistical associations between patient genetics and anti-insulin ADA could be taken into account when developing new versions of marketed insulins. In another instance, comparison of the ADA incidence for drugs with different mutations may suggest what protein modifications are more likely to increase the risk of unwanted immunogenicity. In another embodiment, the databases can be used to identity protein epitopes involved in tolerance induction. Furthermore, database clinical data obtained for antibody epitope mapping could further indicate regions of the drug more likely to be immunogenic. In the course of new product development, human subjects enrolled in clinical trials could be monitored with the portable device for ADA development, and the database consulted to compare ADA incidence for the new drug.

Postmarketing surveillance for therapeutic drugs could also utilize the present invention. A major challenge with postmarketing ADA detection is lack of uniformity of the different assays used, which preclude reliable comparisons between different drugs. The portable device of the present invention, when used at a point of care (for example a physician's office, hospital, urgent care or similar), would become part of the patient's records (amenable to being incorporated into "big data" analysis). Besides, it would be a standard assay, allowing reliable comparisons between various insulin drugs. That could also include comparisons for biosimilar insulins, which follow an expedited development pathway, and whose long-term immunogenicity potential is often expected to be evaluated postmarketing.

In FIG. 4, the first column lists some insulin therapies approved for treatment of type 1 diabetes. Other variants and formulations, including but not restricted to biosimilars can also be added. By clicking on the therapy name, the user can access a link with additional information for each therapy, including but not restricted to route of administration, frequency of administration, dose, reported side-effects, and reported efficacy at the dose tested. Similar to the organization of the first column, by clicking on links available in other columns the user may obtain additional information. The second column lists the incidence of anti-insulin ADA obtained in studies using an ADA testing device of the present invention, which can allow direct comparison between drugs. The third column provides associations (or lack thereof) between MHC class II haplotypes and anti-insulin ADAs. The fourth column includes information about the molecular entities, including but not restricted to any protein engineering that may lead to changes in the biophysical properties. The fifth column lists relevant "chemistry, manufacturing and control" (CMC) factors.

Example 3

Figure 2A:
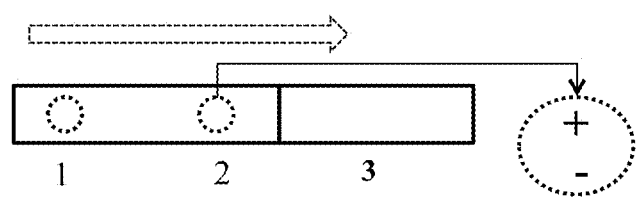
FIG. 2A. Non-limiting example of a portable device to detect anti-drug antibodies (ADAs) of the IgG type. Individual portable devices enable (but are not restricted to) patient self-testing and/or point of care testing. Other formats can also be used. Test-sample (blood, serum, plasma or other source) is added and at position "1", and ADAs bind labeled anti-IgG present in the matrix. The IgG-anti-IgG complexes migrate by "lateral flow" towards the immobilized test protein and positive control (position "2"). When the sample reaches the test region, a defined pattern is displayed at position "2": −, no IgG detected; ±, IgG detected. Position "3" has a waste reservoir or open end. A similar device can be used for IgM detection, in which case labeled anti-IgM is used to generate signal. A similar device can also be used for the detection of other ADAs besides IgG and IgM. Test components may be assembled in various formats, and they may also be mounted inside cases of different designs.
Figure 2B:
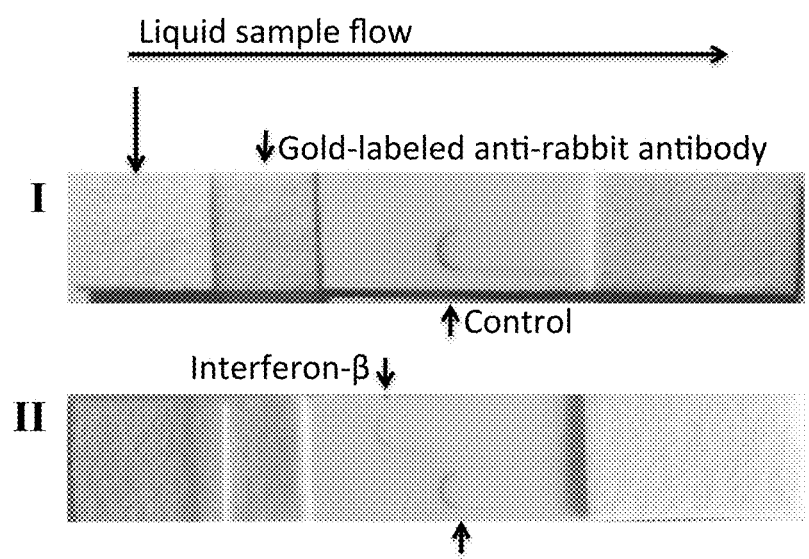
FIG. 2B. Laboratory data obtained with a portable device that detects anti drug antibodies (ADAs). Individual portable devices enable (but are not restricted to) patient self-testing and/or point of care testing. The interior sections of this non-limiting example are shown, and consist of a sample pad, a conjugate pad, a nitrocellulose membrane and an absorbent pad. The conjugate pad was impregnated with a goat gold-labeled anti-rabbit IgG polyclonal antibody. The control consisted of anti-goat IgG polyclonal antibody, immobilized on the nitrocellulose membrane. When the sample (rabbit anti-interferon-β polyclonal antibody) is loaded on the sample pad, the liquid flows towards the conjugate pad, antibodies binds to the gold-labeled antibodies, and subsequently to the membrane-immobilized proteins in a selective manner, generating a signal. (I) Only the control was immobilized on the membrane, in the position indicated by the arrow; (II) Arrows indicate the signal in the positions where either interferon-β or control were immobilized on the membrane.
Figure 2C:
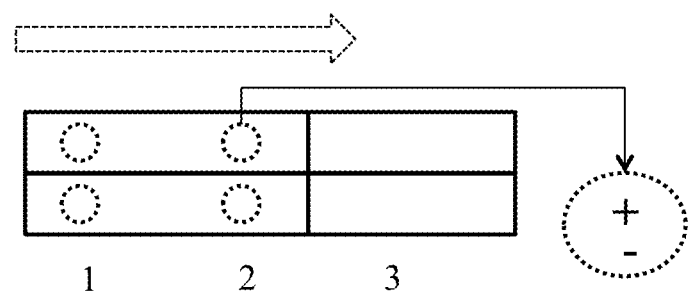
FIG. 2C. Non-limiting example of a portable device for detection of both IgG and IgM, which uses the features described in FIG. 2A above, but with both labeled anti-IgG and labeled anti-IgM present in the matrix and samples running on parallel channels. Additional immunoglobulins can also be detected in additional channels. Individual portable devices enable (but are not restricted to) patient self-testing and/or point of care testing.
Figure 2D:
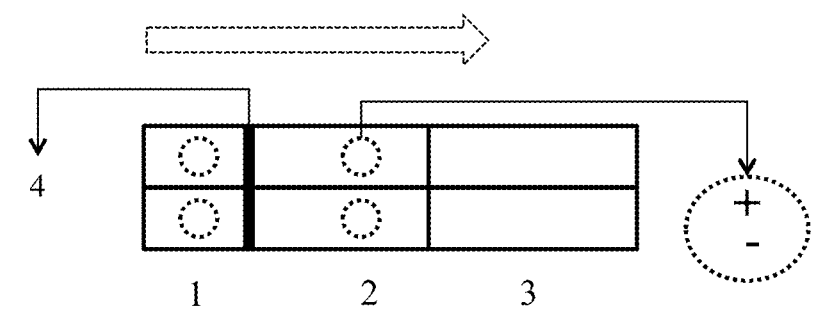
FIG. 2D. Portable devices as described in FIG. 2A and FIG. 2C above, in which a filter is added after position "1" for additional separation of cells and/or other debris. Alternatively, the sample pad can be adapted to perform a filtration step.
Figure 2E:
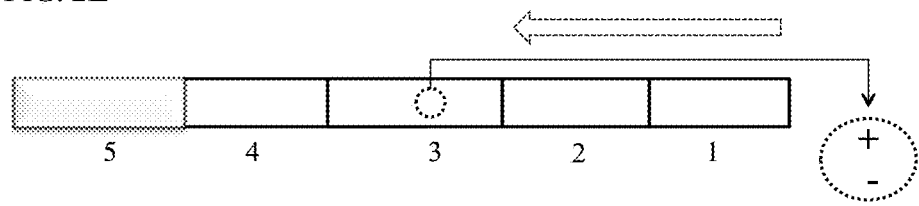
FIG. 2E. Portable device for ADA detection (IgG and/or IgM and/or other ADAs). The sample is placed in a sample pad at position "1", and a handle may be placed on the opposite side (position "5"). The ADAs in the test sample migrate towards a secondary antibody conjugated with a label, available at position "2" in the matrix. The sample ADAs are bound to the labeled secondary antibodies, and the complexes migrate towards position "3", where they are captured by the test protein immobilized on the membrane, resulting in a signal. Position "4" may have a waste reservoir.
Figure 2F:
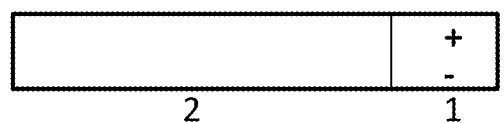
FIG. 2F. Test strip for ADA detection. Sample is added to position "1" of the test strip, where the test protein (+) is immobilized. The strip is held at position "2". Labeled anti-IgG and/or anti-IgM can be added prior or after sample addition, or may be embedded in the matrix, allowing signal development. A wash step may be used to eliminate background. A signal reader can also be used to measure the resulting signal.
Figure 2G:
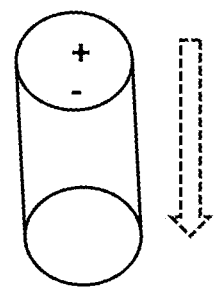
FIG. 2G. Portable device for ADA detection in which the sample is subjected to vertical flow, for example due to gravity.

Use of Portable Devices for Anti-Drug Antibody (ADA) Testing at a Point of Care (for Example Physician's Office) or by a Patient FIG. 2A, FIG. 2B, FIG. 2C, FIG. 2D, FIG. 2E, FIG. 2F, and FIG. 2G provide several non-limiting examples of portable devices that can be used for detecting ADA in body fluids and/or tissues. More specifically, FIG. 2B shows a non-limiting example of the interior of a device used to test anti-IFN-$\beta$ ADAs, consisting of a sample pad, followed by a conjugate pad, a membrane and an absorbent pad. In this case, the sample consisted of rabbit anti-human IFN-$\beta$ ADAs; gold-labelled anti-rabbit was placed on the conjugate pad, and a control (anti-goat IgG) or human IFN-$\beta$ immobilized on the membrane. As the sample flows towards the absorbent pad, the gold-labeled goat anti-rabbit antibodies bind to the constant region of the rabbit anti-IFN-$\beta$ ADAs, which subsequently bind to the immobilized IFN-$\beta$, where the signal is generated. By changing the drug immobilized on the membrane and the labelled anti-ADA antibodies, ADAs against several other therapeutic drugs can be tested with a similar strategy. For instance, human insulin can be immobilized on a membrane and labelled anti-human antibodies placed on the conjugate pad, allowing for the detection of human anti-insulin antibodies. For point of care testing, the sample can be body fluids such as serum, plasma or blood. For patient self-testing the sample can be, for example, one blood drop obtained using a lancet. In another embodiment, the portable device can contain a code or another means of allowing access to a database related to the therapeutic drug.

In another embodiment, the membrane can have immobilized distinct regions of the therapeutic protein, and/or peptides, allowing for antibody epitope mapping. This can help guide treatment selection. For example, if it is determined that the ADAs are directed toward one specific mutated region in a modified version of a therapeutic protein, the same biotherapeutic without that mutation may represent a more suitable treatment option.

What is claimed is:

1. A method for assessing risks associated with human immune responses against therapeutic drugs, the method comprising:

a. Contacting a biological sample from a human subject with a portable device capable of testing for human anti-drug antibodies (ADAs) against one or more therapeutic drugs, wherein labeled entities are immobilized on the portable device, wherein said labeled entities on said device can bind to a constant region of the human ADAs and wherein the labeled entities bound to ADAs complex flow towards to one or more capture reagent immobilized on the device, and wherein the capture reagent comprises said therapeutic drugs or regions of said therapeutic drugs;

b. Detecting a visible signal resulting from binding of ADAs from step (a) to one or more therapeutic drugs or regions of said therapeutic drugs immobilized on the device; and c. Correlating signal from step (b) with presence or absence of ADAs.

2. The method of claim 1, wherein a code on the portable device allows access to a database, and wherein the database comprises ADA data obtained from other human subjects, using the same portable device of claim 1.

3. The method of claim 2, wherein the database comprises genetic analyses of human patients, and their associations with human ADA responses or immune tolerance, and wherein ADA data used to test said associations comprise ADA data obtained with the portable device of claim 1.

4. The method of claim 2, wherein the database comprises data from human patients with one or more of the following: autoimmune disease; diabetes; multiple sclerosis; rheumatoid arthritis; cancer; cardiovascular disease; other diseases for which treatment can include a therapeutic drug, wherein the drug is a protein or peptide, alone or conjugated with a chemical entity or moiety.

5. The method of claim 2, wherein the database contains information for one or more of the following therapeutic drugs: insulin, native or modified; interferon-β, native or modified; therapeutic antibody; enzyme replacement therapy; a therapeutic drug for other applications, wherein the drug is a protein or peptide, alone or conjugated with a chemical entity or moiety.

6. The method of claim 2, wherein the database is combined with other databases, and has differential levels of access and security.

7. The method of claim 2, wherein the database provides information for one or more of the following: to assess the likelihood of host anti-drug antibody responses; to assess likelihood of host neutralizing antibody responses; to predict drug efficacy; to predict drug safety; to guide therapy selection; to assess likelihood of adverse reactions upon administration of a therapeutic drug to a patient or animal model; to estimate an effective therapeutic drug dose; to obtain scientific guidance for engineering of biotherapeutics; to engineer less immunogenic proteins; to obtain scientific guidance for drug discovery; to obtain scientific guidance for drug development; for postmarketing surveillance of therapeutic drugs.

8. The method of claim 2, wherein the database contains ADA data obtained with said portable device, and comparisons with data obtained with other ADA assays.

9. The method of claim 2, wherein the database is used to compare therapeutic drugs and gene therapy within a given therapeutic area, wherein gene therapy comprises correction of a genetic defect in a human patient, and wherein the incidence of human ADAs against a therapeutic protein drug is compared with the incidence of human antibodies against the same protein following gene therapy.

10. The method of claim 2, wherein the database is used to evaluate therapeutic drugs, with analysis of patient megadata (big data), for applications including one or more of the following: testing the effect of anti-drug antibodies and their possible associations with the etiology of diseases; testing the influence of genetic components in ADA responses; guiding discovery of novel therapeutic drugs; guiding development of novel therapeutic drugs; comparing therapeutic drugs for efficacy; comparing therapeutic drugs for safety.

11. The method of claim 2, wherein the database provides guidance for therapeutic drug ranking and selection.

* * * * *